United States Patent [19]

Chikuma

[11] Patent Number: 5,591,156
[45] Date of Patent: Jan. 7, 1997

[54] SEMICONDUCTOR MEDICAL TREATMENT INSTRUMENT

[76] Inventor: Toichi Chikuma, 4-11-9-703, Sendagaya, Shibuya-ku, Tokyo, 151, Japan

[21] Appl. No.: 977,968

[22] Filed: Nov. 18, 1992

[51] Int. Cl.⁶ .......................... A61B 17/00; A61B 17/38
[52] U.S. Cl. .................................. 606/1; 606/41
[58] Field of Search .......................... 606/1; 128/419 R, 128/420.5, 783, 794, 795, 796; 607/46, 47, 49

[56] References Cited

U.S. PATENT DOCUMENTS

| | | | |
|---|---|---|---|
| 3,629,521 | 12/1971 | Puharich | 128/1 R |
| 4,572,194 | 2/1986 | Head | 128/419 R |

FOREIGN PATENT DOCUMENTS

| | | | |
|---|---|---|---|
| 56-150553 | 11/1981 | Japan. | |
| 2129243 | 5/1984 | United Kingdom | 607/46 |

OTHER PUBLICATIONS

Japanese Medical Guidance (Nihon of Ido), No. 421 and 422.
Part 1, Chapter 1, "Measurement Technique for Medical Treatment" (Iryou–you Keisoku Gijutu).

*Primary Examiner*—Angela D. Sykes
*Assistant Examiner*—Sonya Harris
*Attorney, Agent, or Firm*—Lowe, Price, LeBlanc & Becker

[57] ABSTRACT

A semiconductor medical treatment instrument in close contact with a part of the human body at which a pain is caused. A plurality of sets of diodes in each of which two diodes the same in kind as each other are arranged in parallel relation to each other such that a direction extending from an anode to a cathode of one of the diodes is opposite a direction extending from an anode to a cathode of the other diode are arranged such that the directions connecting respectively the anodes and the cathodes to each other extend perpendicularly to each other.

8 Claims, 4 Drawing Sheets

SEMICONDUCTOR MEDICAL TREATMENT INSTRUMENT

BACKGROUND OF THE INVENTION

The present invention relates to a semiconductor medical treatment instrument.

A semiconductor diode is utilized to execute both mitigation or reduction in a pain such as a stiffness in the shoulders, lumbago or a crick in the back, a muscular pain and the like. It has been described in "Japanese Medical Guidance (Nihon of Ido), No. 421 and No. 422 (publication from Japanese Medical Guidance (Nihon of Ido)) and the like that the above-described both methods have a certain degree of analgesic advantages.

On the other hand, as described in Part 1, Chapter 1 of "Measurement Technique for Medical Treatment (Iryou-you Keisoku Gijutu) (publication from Corona-sha), bioelectric current having an irregular waveform flows through the human body. Particularly, it has been considered that harmful bioelectric current flows through a pain portion.

Accordingly, it will be reasonable or appropriate to consider that analgesic effects produced by a method of treatment like one described above are based on the rectification of the semiconductor diode.

However, if a simple semiconductor diode is used as it is, medical treatment effects are thin or low, and effects are different from each other depending upon directions to a cathode and an anode of the diode.

In view of the above, the following apparatus for medical treatment due to a metallic-pack of a plurality of diodes has been proposed in Japanese Utility Model Laid-Open No. 150553/1981. That is, cathode lead wires and anode lead wires of two (2) diodes are packed in both sides by a metallic plate having an area of approximately 4 cm$^2$. Anode lead wires and cathode lead wires on the opposite side are cut off and are located adjacent respectively to the anode lead wires and the anode lead wires on the one side, to leave slightly exposed portions.

However, the above-described arrangement has the following defect or disadvantage. That is, the arrangement in which two (2) diodes are arranged in parallel relation to the direction only neutralizes the bioelectric current in one direction. Accordingly, the medical treatment effects are different from each other depending upon a pasting-up or sticking direction of the diodes with respect to the bioelectric current. Thus, it is difficult to look for or seek for an adequate sticking location and a sticking direction. If the number of sticking does not increase, the effects are thin or ineffective.

SUMMARY OF THE INVENTION

It is an object of the invention to provide a semiconductor medical treatment instrument which is advantageous in medical treatment regardless of a sticking direction, which is easy in a using method, and which is high in medical treatment effects per one instrument.

According to the invention, there is provided a semiconductor medical treatment instrument in which a plurality of sets of diodes in each of which two diodes the same in kind as each other are arranged in parallel relation to each other such that directions extending from cathodes to anodes thereof are opposite to each other are arranged such that a direction connecting the cathode and the anode of one of the diodes to each other extend perpendicularly to a direction connecting the cathode and the anode of the other diode.

Each set of diodes may be arranged such that both ends of each of the diodes are insulated, or both ends of one of the diodes are connected respectively to both ends of the other diode. Alternatively, each set of diodes may be arranged such that one ends of the respective diodes are connected to each other and the other ends thereof are insulated.

Each set of diodes may be arranged such that a direction extending between a cathode of one of the diodes and an anode of the other diode to each other extends along a direction of each of two or three axes extending perpendicularly to each other.

Each diode may be embedded in a retainer, and the retainer may be stuck to an adhesive layer of a sticking sheet. Alternatively, a protective sheet may be mounted on an upper surface of the retainer.

It has been considered that an abnormal quantity of electricity due to a pain generated from muscles, a stiffness is the sum total of vectors of the bioelectric currents which are generated from locations at which these pain and stiffness occur. Since the abnormal electricity can be dissolved or decomposed into vectors in three directions extending perpendicularly to each other, the abnormal electricity in the three vector directions are perfectly neutralized and extinguished in the set of three diodes in which the directions connecting the cathode and the anode to each other extend perpendicularly to each other.

In fact, since the semiconductor medical treatment instrument is stuck to a body surface, sufficient medical treatment effects can be produced if the directions connecting the cathodes and the anodes of the respective sets of two diodes to each other are provided perpendicularly to each other, if the sets of diodes are mounted in insertion on the body surface in parallel relation to each other, and if the vectors of the abnormal electricity flowing through the body surface in two directions extending perpendicularly to each other are neutralized and extinguished by the diodes.

DESCRIPTION OF THE PREFERRED EMBODIMENTS OF THE INVENTION

Figure 1:
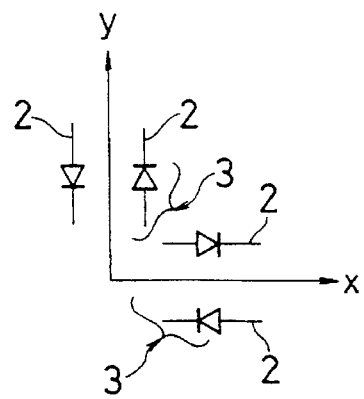
FIG. 1 is an arrangement view of a semiconductor of a semiconductor medical treatment instrument according to a first embodiment of the invention.

FIG. 1 shows an arrangement of diodes in a first embodiment of a semiconductor medical treatment instrument 1. Two sets of diodes 3 arranged such that directions extending from cathodes of each set of two diodes 2 the same in kind as each other toward anodes thereof are arranged antiparallel orientation, i.e., in parallel relation to each other and in opposed relation to each other, and are arranged such that the directions connecting the cathodes and the anodes to each other extend respectively along two coordinate axes x and y extending perpendicularly to each other.

Figure 2:
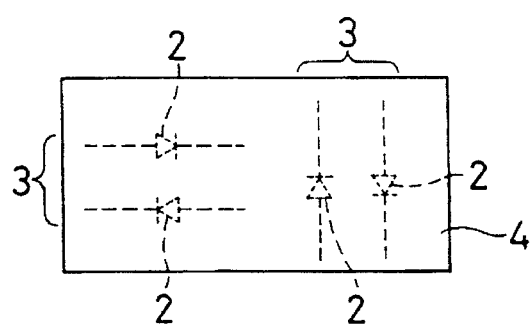
FIG. 2 is a top plan view of a retainer.

Each set of two diodes 3 is arranged such that both terminals of each of the diodes 2 are insulated. As shown in FIG. 2, each set of two diodes 3 is embedded in or laid under a retainer 4 which is made of an electric insulator such as synthetic resin or the like.

Figure 3:
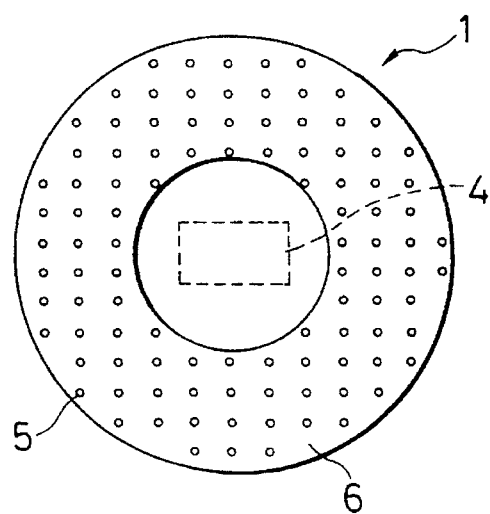
FIG. 3 is a top plan view of the semiconductor medical treatment instrument.
Figure 4:
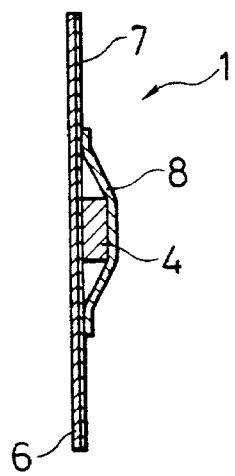
FIG. 4 is a cross-sectional view of FIG. 3.

As shown in FIGS. 3 and 4, the retainer 4 is made of soft synthetic resin, and is stuck onto an adhesive layer 7 which is applied to one side of a circular sticking sheet 6 formed therein with a plurality of through bores 5. A protective sheet 8 made of metal, paper, synthetic resin or the like is stuck onto an upper surface of the adhesive layer 7. Thus, the semiconductor medical treatment instrument 1 is formed.

Figure 5:
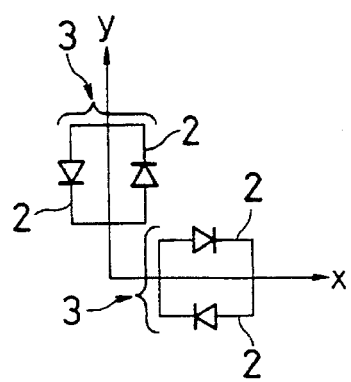
FIG. 5 is an arrangement view of a semiconductor of a semiconductor medical treatment instrument according to a second embodiment of the invention.

FIG. 5 shows an arrangement of diodes according to a second embodiment of the invention. Each of two diodes 2 forming each of the diode assemblies 3 according to the first embodiment have both terminals thereof which are connected to each other.

Figure 6:
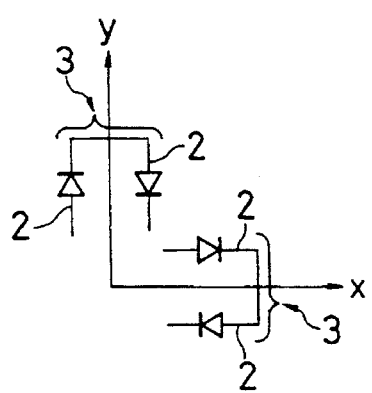
FIG. 6 is an arrangement view of a semiconductor of a semiconductor medical treatment instrument according to a third embodiment of the invention.

FIG. 6 shows an arrangement of diodes according to a third embodiment of the invention, and only one terminals of the two diodes 2 forming each of the diode assemblies 3 according to the first embodiment are connected to each other.

Figure 7:
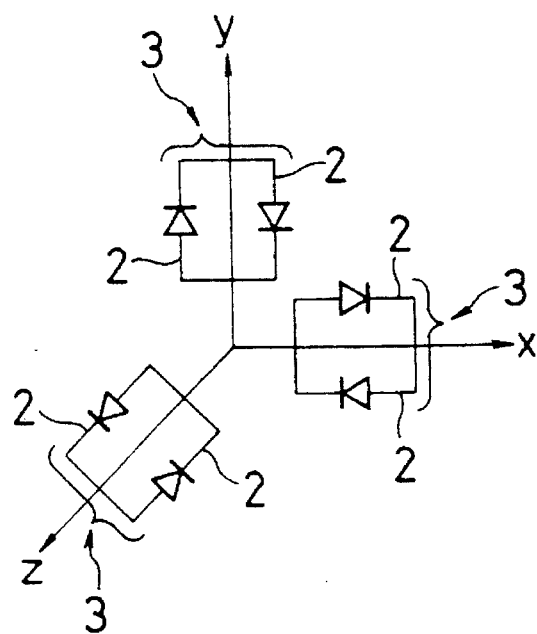
FIG. 7 is an arrangement view of a semiconductor of a semiconductor medical treatment instrument according to a fourth embodiment of the invention.

FIG. 7 shows a fourth embodiment of the invention. Each of diode assemblies 3, in which two diodes 2 the same in kind as each other are arranged in parallel relation to each other in a reverse direction, is arranged such that a direction connecting an anode and a cathode to each other of the diode assembly 3 extends along a corresponding one of three coordinate axes x, y and z extending perpendicularly to each other.

Figure 8:
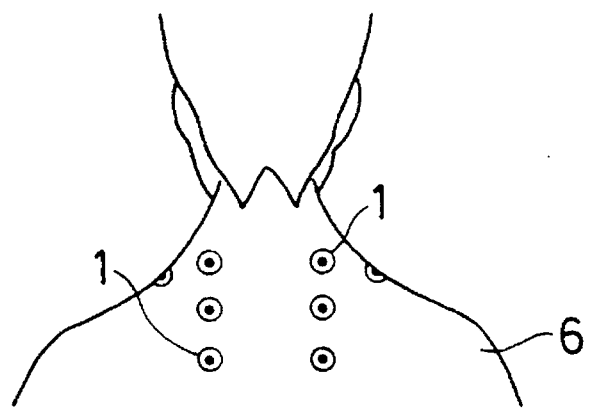
FIG. 8 is a front elevational view showing sticking of the semiconductor medical treatment instrument.

As shown in FIG. 8, the semiconductor medical treatment instruments 1 are arranged such that each retainer 4 is arranged on a pain portion while the protecting sheet 8 is adhered, to stick the adhesive layer 7 of the sticking sheet 6 to a skin of the human body.

The semiconductor medical treatment instrument according to the invention is arranged such that the sets of diodes in each of which the two diodes the same in kind as each other are arranged in parallel relation to each other with the directions extending from the cathodes to the anodes of the respective diodes extending in opposite directions to each other are arranged such that the direction connecting the cathode and the anode of one of the set to the direction connecting the cathode and the anode of the other of the sets extends perpendicularly thereto. Accordingly, by the sets of diodes, the vector in the direction connecting the cathode and the anode of one of the sets to each other of the abnormal electricity which is generated from an abnormal part of the human body to each other is neutralized. For this reason, the abnormal electricity is completely or perfectly distinguished regardless of the direction connecting the cathode and the anode of each of the sets of diodes to each other so that a pain and a stiffness can be relieved. Mounting with respect to the human body is easy. It is possible to produce medical treatment effects in what manner the semiconductor medical treatment instrument 1 is stuck.

Figure 9:
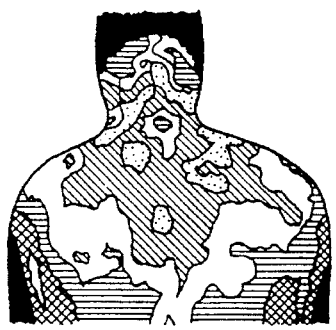
FIGS. 9 to 11 are views showing a change in body surface temperature due to sticking of a conventional semiconductor medical treatment instrument.
Figure 10:
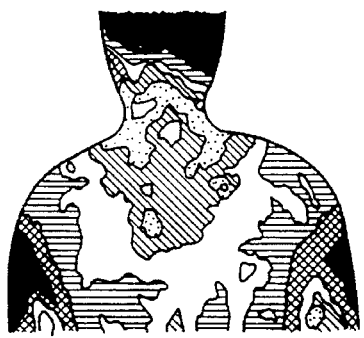
Figure 11:
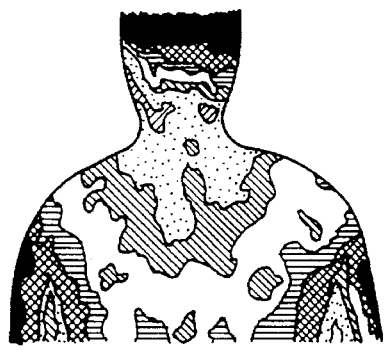

If the above-described effects are indicated by data, FIG. 8 is formed. As shown in FIG. 8, in each of the semiconductor medical treatment instruments 1, having a plurality of sets of diodes, in each of which the two diodes are arranged in opposite parallel relation to each other in a case where the semiconductor medical treatment instrument 1 is stuck to the human body 6, the body surface temperature indicated in FIG. 9 is shown prior to sticking. However, after thirty (30) minutes, the body surface temperature shifts or is changed to that illustrated in FIG. 10. Further, after sixty (60) minutes, the body surface temperature is changed to that illustrated in FIG. 11.

Figure 12:
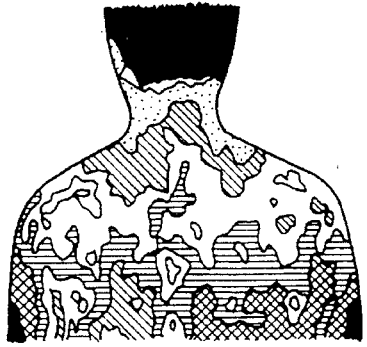
FIGS. 12 to 14 are views showing a change in body surface temperature due to sticking of the semiconductor medical treatment instrument according to the invention.
Figure 13:
Figure 14:
Figure 15:
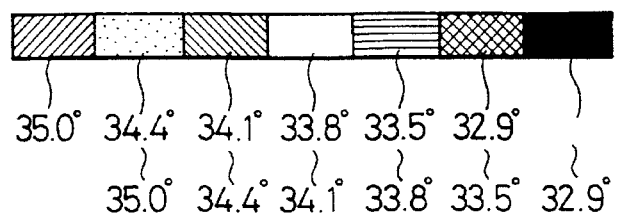
FIG. 15 is a view showing temperature ranges illustrated in FIG. 9 to FIG. 11.

On the contrary, in the semiconductor medical treatment instrument according to the invention, the body surface temperature before sticking was as shown in FIG. 12 and FIG. 15. However, on thirty (30) minutes after sticking, the body surface temperature changes as shown in FIG. 13 and FIG. 15, and changes as shown in FIGS. 14 and 15 on sixty (60) minutes after sticking. It will be apparent that a rising rate of the body temperature is large.

What is claimed is:

1. A semiconductor medical treatment instrument, comprising:

a first diode set having a first diode and a second diode in an antiparallel orientation relative to each other; and a second diode set having a third diode and a fourth diode in an antiparallel orientation relative to each other, said third and fourth diodes being disposed orthogonally with respect to said first and second diodes.

2. A semiconductor medical treatment instrument according to claim 1, wherein:

a cathode and an anode of said first diode are insulated from a cathode and an anode of said second diode.

3. A semiconductor medical treatment instrument according to claim 1, wherein:

a cathode and an anode of said first diode are connected, respectively, to an anode and a cathode of said second diode.

4. A semiconductor medical treatment instrument according to claim 1, wherein:

a cathode of said first diode is connected to an anode of said second diode and an anode of said first diode is insulated from a cathode of said second diode.

5. A semiconductor medical treatment instrument according to claim 1, further comprising:

a third diode set having a fifth and a sixth diode in an antiparallel orientation relative to each other, said third diode set being disposed orthogonally with respect to each of said first and second diode sets, whereby said first, second and third diode sets are disposed along three axes perpendicularly to each other.

6. A semiconductor medical treatment instrument according to claim 1, wherein:

each diode is embedded in a retainer comprising an electrically insulating material.

7. A semiconductor medical treatment instrument according to claim 6, wherein:

said retainer is stuck to a sheet having an adhesive layer.

8. A semiconductor medical treatment instrument according to claim 7, wherein a protective sheet is mounted on an upper surface of said retainer.

* * * * *